(12) United States Patent
Lohray et al.

(10) Patent No.: US 7,732,608 B2
(45) Date of Patent: Jun. 8, 2010

(54) SALTS OF CLOPIDOGREL AND PROCESS FOR PREPARATION

(75) Inventors: Braj Bhushan Lohray, Gujarat (IN); Vidya Bhushan Lohray, Gujarat (IN); Mayank Ghanshyambhai Dave, Gujarat (IN)

(73) Assignee: Cadila Healthcare Limited, Gujarat (IN)

( * ) Notice: Subject to any disclaimer, the term of this patent is extended or adjusted under 35 U.S.C. 154(b) by 829 days.

(21) Appl. No.: 10/554,367

(22) PCT Filed: Apr. 22, 2004

(86) PCT No.: PCT/IN2004/000112

§ 371 (c)(1),
(2), (4) Date: Feb. 1, 2006

(87) PCT Pub. No.: WO2004/106344

PCT Pub. Date: Dec. 9, 2004

(65) Prior Publication Data

US 2006/0264636 A1    Nov. 23, 2006

(30) Foreign Application Priority Data

Apr. 25, 2003   (IN) ...................... 413/MUM/2003

(51) Int. Cl.
*C07D 513/02* (2006.01)

(52) U.S. Cl. .................................................. 546/114

(58) Field of Classification Search .................. 546/114
See application file for complete search history.

(56) References Cited

U.S. PATENT DOCUMENTS

| 4,529,596 A | 7/1985 | Aubert et al. |
| 4,847,265 A | 7/1989 | Badorc et al. |
| 6,429,210 B1 | 8/2002 | Bousquet et al. |
| 6,509,348 B1 | 1/2003 | Ogletree |
| 6,635,763 B2 | 10/2003 | Pandey et al. |
| 6,767,913 B2 | 7/2004 | Lifshitz et al. |
| 2002/0177712 A1 | 11/2002 | Pandey et al. |
| 2005/0203122 A1 | 9/2005 | Doser et al. |
| 2005/0256152 A1 | 11/2005 | Doser et al. |
| 2006/0264636 A1 | 11/2006 | Lohray et al. |
| 2007/0037842 A1 | 2/2007 | Lohray et al. |
| 2007/0082924 A1 | 4/2007 | Lohray |
| 2009/0270448 A1 | 10/2009 | Rey et al. |

FOREIGN PATENT DOCUMENTS

| EP | 1900358 | 3/2008 |
| WO | 2004/013147 | 2/2004 |
| WO | 2004/072084 A | 8/2004 |
| WO | 2004/072085 A | 8/2004 |
| WO | 2004/074215 A | 9/2004 |

OTHER PUBLICATIONS

Caira, "Crystalline Polymorphism of Organic Compounds", Topics in Current Chemistry, vol. 198, 1998, pp. 163-208, XP001156954.
Exhibit 1—Rosenberg, *Patent Law Basics*, West Group, pp. 9-58 and 9-59 (2000).
Exhibit 2—*Fiers v. Sugano* 25 USPQ2d 1601, seven pages (Fed. Cir. 1993).
Exhibit 3—Rosenberg, *Patent Law Basics*, West Group pp. 9-62 and 9-63 (2000).
Exhibit 4—Rosenberg, *Patent Law Basics*, West Group pp. 9-30 and 9-31 (2000).
Exhibit 5—Byrn et al. "Solid-state pharmaceutical chemistry" *Chem. Mater.*, vol. 6, pp. 1148-1158 (1994).
Exhibit 6—Byrn et al. *Solid-State Chemistry of Drugs*, Academic Press, pp. 3-27 (1982).
Exhibit 7—Dunitz et al. "Disappearing polymorphs" *Acc. Chem. Res.*, vol. 28, pp. 193-200 (1995).
Exhibit 8—Knapman "Polymorphic prediction" *Modern Drug Discovery*, vol. 3, pp. 53-54 and 57, four sheets (2000).
Exhibit 9—Stability Report for Clopidogral besylate Substance, one sheet (2008).
Written Opinion of PCT/IN2004/000112, eight pages, mailed Jan. 25, 2005.

*Primary Examiner*—Janet L. Andres
*Assistant Examiner*—Raymond Covington
(74) *Attorney, Agent, or Firm*—Nixon & Vanderhye P.C.

(57) ABSTRACT

Disclosed are salts of Clopidogrel viz. Clopidegrel mesylate, Clopidegrel besylate and Clopidogrel tosylate, methods for their preparation and pharmaceutical compositions containing them and their use in medicine.

9 Claims, 5 Drawing Sheets

SALTS OF CLOPIDOGREL AND PROCESS FOR PREPARATION

This application is the US national phase of international application PCT/IN2004/000112 filed 22 Apr. 2004 which designated the U.S. and claims priority of IN 413/MUM/2003, filed 25 Apr. 2003, the entire contents of each of which are hereby incorporated by reference.

FIELD OF INVENTION

The present invention describes certain salts of Clopidogrel including their hydrates and other solvates, both in amorphous and crystalline forms, processes for their preparation and pharmaceutical compositions containing them and their use in medicine. Clopidogrel is marketed as (S)-(+)-Clopidogrel bisulfate, useful as an antiplatelet drug for the treatment of atherosclerosis, myocardial infarction, strokes and vascular death. The present invention also describes method of treatment of such cardiovascular disorders using the salts of the present invention or mixtures thereof, and pharmaceutical compositions containing them. The present invention also relates to the use of the salts of Clopidogrel disclosed herein and pharmaceutical compositions containing them for the treatment of cardiovascular disorders.

BACKGROUND TO THE INVENTION

The compounds of the invention referred herein, are pharmaceutically acceptable salts of the compound known by its generic name Clopidogrel having structure (I)

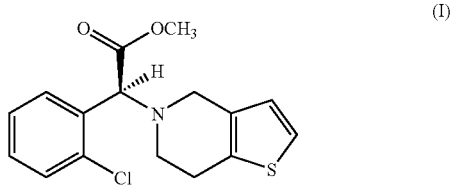

(I)

It is available in the market as its bisulfate salt and is marketed by Sanofi-Synthelabo as "Plavix" having the general formula (II)

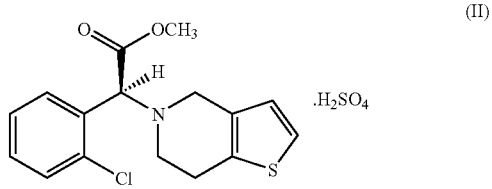

(II)

Clopidogrel is an inhibitor of platelet aggregation and is marketed as an antianginal agent, antiplatelet agent and is found to decrease morbid events in people with established atherosclerotic cardiovascular disease and cerebrovascular diseases.

The therapeutic application of Clopidogrel as blood-platelet aggregation inhibiting agents and antithrombotic agent and its preparation is disclosed in U.S. Pat. Nos. 4,529,596. 4,847,265 describes the process for the preparation of the hydrogen sulfate salt of Clopidogrel.

Polymorphs of Clopidogrel bisulfate has been described in U.S. Pat. Nos. 6,504,040 and 6,429,210. We have disclosed novel polymorphs of Clopidogrel bislufate in our PCT International Application No. PCT/IN03/00053.

The present applicant has also disclosed novel processes for preparing Clopidogrel base in U.S. Pat. No. 6,635,763.

U.S. Pat. No. 4,847,265 discloses that the dextrorotatory enantiomer of formula (I) of Clopidogrel has an excellent antiagregant platelet activity, whereas the corresponding levorotatory enantiomer of Formula (I) is less tolerated of the two enantiomers and is less active. U.S. Pat. No. 4,847,265 also describes various other salts of the compound of formula (I), like its hydrochloride, carboxylic acid and sulfonic acids salts. Specifically, salts of acetic, benzoic, fumaric, maleic, citric, tartaric, gentisic, methanesulfonic, ethanesulfonic, benzenesulfonic and lauryl sulfonic acids were prepared. However, according to this patent, these salts usually precipitated in amorphous form and/or they were hygroscopic making them difficult to handle in an industrial scale. Also, no data corresponding to any of these salts are reported. The specification also describes salts of dobesilic acid (m.p.=70° C.) and para-toluenesulfonic acid, having a melting point of 51° C., the purification of which, as accepted in the patent, proved to be difficult.

Thus, there remains a need to prepare salts of Clopidogrel which are stable, easy to handle, can be purified and can be exploited on an industrial scale.

We hereby disclose certain pharmaceutically acceptable salts of Clopidogrel particularly the salts of p-toluenesulfonic acid, benzenesulfonic acid and methanesulfonic acids both in crystalline and amorphous forms, including their hydrates and other solvates which are well characterized, free flowing, easy to handle and having high purity.

OBJECTS OF THE INVENTION

It is therefore, an object of the present invention to prepare new pharmaceutically acceptable salts of Clopidogrel. More particularly, the present invention aims to provide new forms of Clopidogrel p-toluenesulfonate, Clopidogrel benzenesulfonate and Clopidogrel methanesulfonate, including their hydrates and other solvates in both crystalline and amorphous forms.

Another object of the present invention is to provide processes for preparing the new salts described herein.

A further object of the present invention is to provide the salts in pure, easy to handle, free flowing and stable form.

A further object is to provide a process of preparation of the pharmaceutically acceptable salts of the present invention on an industrial scale.

It is also an object of the present invention to provide for pharmaceutical compositions of the pharmaceutically acceptable salts of Clopidogrel of the present invention, as described herein.

Another object is to provide a method of treatment of cardiovascular disorders, comprising administering, for example, orally a composition containing the pharmaceutically acceptable salts of the present invention in a therapeutically effective amount.

SUMMARY OF THE INVENTION

The present invention describes certain pharmaceutically acceptable salts of Clopidogrel including their hydrates and other solvates, both in crystalline and amorphous forms, processes for their preparation and pharmaceutical compositions containing them and their use in medicine. More particularly, the present invention describes new forms of Clopidogrel p-toluenesulfonate (or Clopidogrel tosylate), Clopidogrel benzenesulfonate (or Clopidogrel besylate) and Clopidogrel methanesulfonate (or Clopidogrel mesylate). Also described are processes for their preparation and pharmaceutical compositions containing the same and their use in medicine.

DETAILED DESCRIPTION

Figure 1:
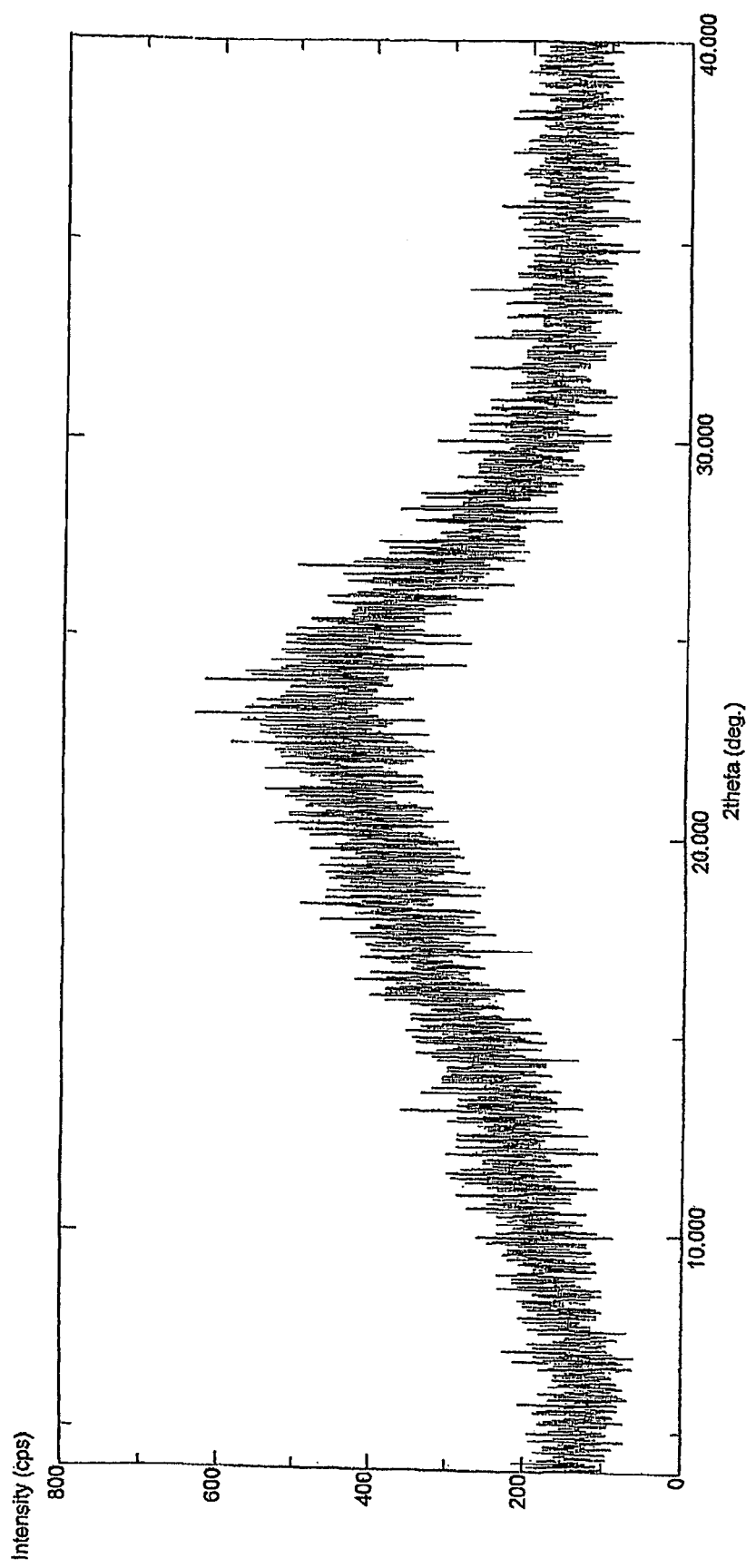
FIG. 1: XRD of amorphous Clopidogrel besylate

The present invention provides certain pharmaceutically acceptable salts of Clopidogrel having the general formula (III) given below:

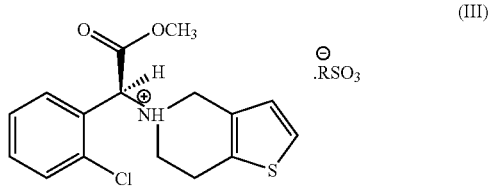

wherein R represents 4-methylphenyl, phenyl or a methyl group.

More particularly, the present invention describes stable forms of Clopidogrel p-toluenesulfonate, Clopidogrel benzenesulfonate and Clopidogrel methanesulfonate. These salts in their hydrated or other solvated forms is also encompassed within the present invention. The salts may be present either in crystalline or amorphous form. The salts may be prepared by reacting Clopidogrel base with the corresponding acids (p-toluenesulfonic acid, benzenesulfonic acid and methanesulfonic acid respectively) in a suitable solvent, at a temperature ranging from −30° C. to 50° C., and subsequently, removing the solvent. The suitable solvents can be water, methanol, ethanol, acetone, propanol, n-butanol, n-pentanol, n-hexanol, n-heptanol, dichloromethane, dimethyl formamide, dimethyl acetamide, 1,4-dioxane, tetrahydrofuran, ether, hexane, heptane, acetonitrile or mixtures thereof The removal of the solvent can be done preferably at reduced pressure.

In a preferred embodiment, the Clopidogrel base may be prepared according to the processes disclosed in U.S. Pat. No. 6,635,763.

The salts may exist in a solvent-free form or it may be isolated as a hydrate or a solvate. The hydrates and solvates of the salts of the present invention form another aspect of the invention.

The salts can be characterized by suitable techniques known in the art.

The amorphous Clopidogrel p-toluene sulfonate (Clopidogrel tosylate) has a melting point in between the range of 70-95° C.

The amorphous Clopidogrel benzene sulfonate (Clopidogrel besylate) of the present invention has a melting point in between the range of 85° C.-95° C.

The crystalline Clopidogrel benzene sulfonate (Clopidogrel besylate) of the present invention has a melting point in between the range of 124° C.-132° C.

The amorphous Clopidogrel methane sulfonate (Clopidogrel mesylate) has a melting point of in between the range of 60° C.-70° C.

The following non-limiting examples illustrate the inventor's preferred methods for preparing the different salts of S(+) Clopidogrel discussed in the invention and should not be construed to limit the scope of the invention in any way.

EXAMPLE 1

Preparation of Clopidogrel Tosylate Amorphous Form

Clopidogrel base was dissolved in acetone to obtain a clear solution. To it was added p-toluene sulfonic acid at room temperature. The reaction mixture was heated to reflux temperature for 2 to 10 hrs. The solvent was evaporated to dryness under reduced pressure to obtain amorphous Clopidogrel tosylate.
m.p.: 75-93° C. (soften)
XRD: Amorphous
DSC: No melting peak
% water: 0.5-4% by weight (obtained in different batches).

EXAMPLE 2

Preparation of Clopidogrel Tosylate Amorphous Form

Clopidogrel base was dissolved in methanol to obtain a clear solution. To it was added p-toluenesulfonic acid at 20° C. The reaction mixture was heated to reflux temperature for 2 to 10 hrs. The solvent was evaporated to dryness under reduced pressure to obtain a powder.
m. p: 73-93° C. (soften)
XRD: Amorphous
DSC: No melting peak
% water: 0.5-4% by weight (obtained in different batches).

Similarly, the same salt was prepared using THF, acetonitrile and other similar solvents either alone or as a mixture of two or more solvents described elsewhere in the specification.

EXAMPLE 3

Preparation of Clopidogrel Tosylate Amorphous Form

Clopidogrel base was dissolved in methanol. p-Toluene sulphonic acid was added to the solution at 20° C. The reaction mixture was heated to reflux temperature for 2 hrs. The solution was cooled to room temperature and was added drop-wise to diethyl ether. The suspension was stirred at RT. The solid was filtered and dried at about 50° C. in a vacuum oven to give Clopidogrel tosylate similar to that obtained above.

Similarly, same salt was prepared using acetone, acetonitrile and other similar solvents either alone or as a mixture of two or more solvents described elsewhere in the specification.

EXAMPLE 4

Preparation of Clopidogrel Tosylate Amorphous Form

Clopidogrel base was dissolved in methanol. p-Toluene sulphonic acid was added to the solution at 20° C. The reaction mixture was heated to reflux temperature for 2 hrs. The solution was cooled to room temperature and the methanolic solution was added dropwise to hot toluene. The resulting solution was refluxed for an additional 20 minutes. The solution was cooled to room temperature and was stirred for 24 hrs. The solvent was evaporated under reduced pressure to dryness to obtain Clopidogrel tosylate, similar to that obtained above.

Similarly, the same salt was prepared using acetone, acetonitrile and other similar solvents either alone or as a mixture of two or more solvents described elsewhere in the specification.

EXPERIMENT 5

Preparation of Clopidogrel Besylate Amorphous Form

Clopidogrel base was dissolved in acetone to obtain a clear solution. Then benzenesulfonic acid was added to the solution at 20° C. The reaction mixture was heated to reflux temperature for 2 to 10 hrs. The solvent was evaporated to dryness under reduced pressure to obtain the title salt as a powder.

m.p: 86-95° C. (soften)

XRD: Amorphous

DSC: No melting peaks

% water: 0.5-4% by weight. (obtained in different batches).

EXAMPLE 6

Preparation of Clopidogrel Besylate Amorphous Form

Clopidogrel base was dissolved in methanol to obtain a clear solution. Benzenesulfonic acid was added to the solution at 20° C. The reaction mixture was heated to reflux temperature for 2 to 10 hrs. The solvent was evaporated to dryness under reduced pressure to obtain the title compound.

m.p.: 84-93° C. (soften)

XRD: Amorphous

DSC: No melting peak

% water: 0.5-4% by weight (obtained in different batches).

Similarly, the same salt was prepared in THF, acetonitrile and other similar solvents either alone or as a mixture of two or more solvents described elsewhere in the specification.

EXAMPLE 7

Preparation of Clopidogrel Besylate Amorphous Form

Clopidogrel base was dissolved in methanol. Benzene sulphonic acid was added to the solution at 20° C. The reaction mixture was heated to reflux temperature for 2 hrs. The solution was cooled to room temperature and was added drop-wise to diethyl ether. The suspension was stirred at RT. The solid was filtered and dried in a vacuum oven to give Clopidogrel besylate, similar to that obtained above.

Similarly, the same salt was prepared using acetone, acetonitrile and other similar solvents either alone or as a mixture of two or more solvents described elsewhere in the specification.

EXAMPLE 8

Preparation of Clopidogrel Besylate Amorphous Form

Clopidogrel base was dissolved in methanol. Benzene sulphonic acid was added to the solution at 20° C. The reaction mixture was heated to reflux temperature for 2 hrs. The solution was cooled to room temperature and the methanolic solution was added drop-wise to the boiling toluene. The resulting solution was refluxed for an additional 20 minutes. The solution was cooled to room temperature and was stirred at this temperature for extended hours. The solvent was evaporated under reduced pressure to dryness to obtain Clopidogrel besylate, similar to that obtained above.

Similarly, the same salt was prepared using acetone, acetonitrile and other similar solvents either alone or as a mixture of two or more solvents described elsewhere in the specification.

EXAMPLE 9

Preparation of Clopidogrel Besylate Crystalline Form

Clopidogrel besylate amorphous was stirred in diethyl ether at 20° C. The obtained white solid was collected by filtration, washed with diethyl ether and dried, in a vacuum oven to obtain Clopidogrel besylate in crystalline form.

m.p.: 126-130° C. (range obtained from different batches).

XRD: Crystalline

DSC: 127.5-132.9° C.

% water: 0.1-0.3% by weight (range obtained from different batches)

The above process for preparing clopidogrel besylate crystalline form, is carried out using different ethers wherein each alkyl radical of the ether is independently selected from the group consisting of methyl, ethyl propyl, isopropyl, butyl, 1-butyl, 2-butyl and t-butyl or mixtures thereof.

EXAMPLE 10

Preparation of Clopidogrel Besylate Crystalline Form

Clopidogrel besylate amorphous was stirred in n-heptane at 20° C. The obtained white solid was collected by filtration, washed with n-heptane, and dried in a vacuum oven to obtain clopidogrel besylate in crystalline form.

m.p: 125-130° C. (range obtained from different batches).

XRD: Crystalline

DSC: 125.5-130.9° C.

% water: 0.1-0.3% by weight (range obtained from different batches).

Similarly, Clopidogrel besylate crystalline form was prepared in hexane, n-heptane, cyclohexane, petroleum ether as solvents as well as their mixtures.

EXAMPLE 11

Preparation of Clopidogrel Besylate Crystalline Form

Clopidogrel base was dissolved in diethyl ether at 20-25° C. To this was added benzene sulphonic acid dissolved in diethyl ether. The reaction mixture was stirred at 25-30° C. for 24-30 hrs. The white solid was collected by filtration, washed with diethyl ether, and dried at 50-60° C. in a vacuum oven to obtain Clopidogrel besylate crystalline form.
m.p.: 124-130° C. (range obtained from different batches).
XRD: Crystalline
DSC: 128.9-132.7° C.
% water: 0.2%

The above process for preparing clopidogrel besylate crystalline form, is carried out using different ethers wherein each alkyl radical of the ether is independently selected from the group consisting of methyl, ethyl, propyl, isopropyl, butyl, 1-butyl, 2-butyl and t-butyl or mixtures thereof.

EXAMPLE 12

Preparation of Clopidogrel Mesylate Amorphous Form

Clopidogrel base was dissolved in acetone to obtain a clear solution. Methanesulfonic acid was added to the solution at 20° C. The reaction mixture was heated to reflux temperature for 2 to 10 hrs. The solvent was evaporated to dryness under reduced pressure to obtain the title compound.
m.p: 60-70° C. (soften)
XRD: Amorphous
DSC: No melting peak
% water: 0.5-4% by weight (obtained from different batches).

EXAMPLE 13

Preparation of Clopidogrel Mesylate Amorphous Form

Clopidogrel base was dissolved in methanol to obtain a clear solution. Methanesulfonic acid was added to the solution at 20° C. The reaction mixture was heated to reflux temperature for 2 to 10 hrs. The solvent was evaporated to dryness under reduced pressure to obtain the title compound.
m.p: 60-70° C. (soften)
XRD: Amorphous
DSC: No melting peak
% water: 0.5-4% by weight. (obtained from different batches).

Similarly, the same salt was prepared in THF, acetonitrile and other similar solvents either alone or as a mixture of two or more solvents described elsewhere in the specification.

All these salts are free flowing, easy to handle and can be manufactured in large scale as well as can be used in the preparation of suitable pharmaceutical compounds or dosage forms. The salts of the present invention may also exist as different solvates corresponding to the different solvents used in their preparation. Such obvious solvates are also intended to be encompassed within the scope of the present invention.

The salts of Clopidogrel drug substance of the present invention prepared according to any process described above or any other process can be administered to a person in need of it either without further formulation, or formulated into suitable formulations and dosage forms as are well known.

In another embodiment of the present invention a method of treatment and use of the pharmaceutically acceptable salts of Clopidogrel described in the present invention for the treatment of cardiovascular disorders & inhibiting platelet aggregation is provided, comprising administering, for example, orally or in any other suitable dosage forms, a composition containing the new salts of the present invention in a therapeutically effective amount.

Figure 2:
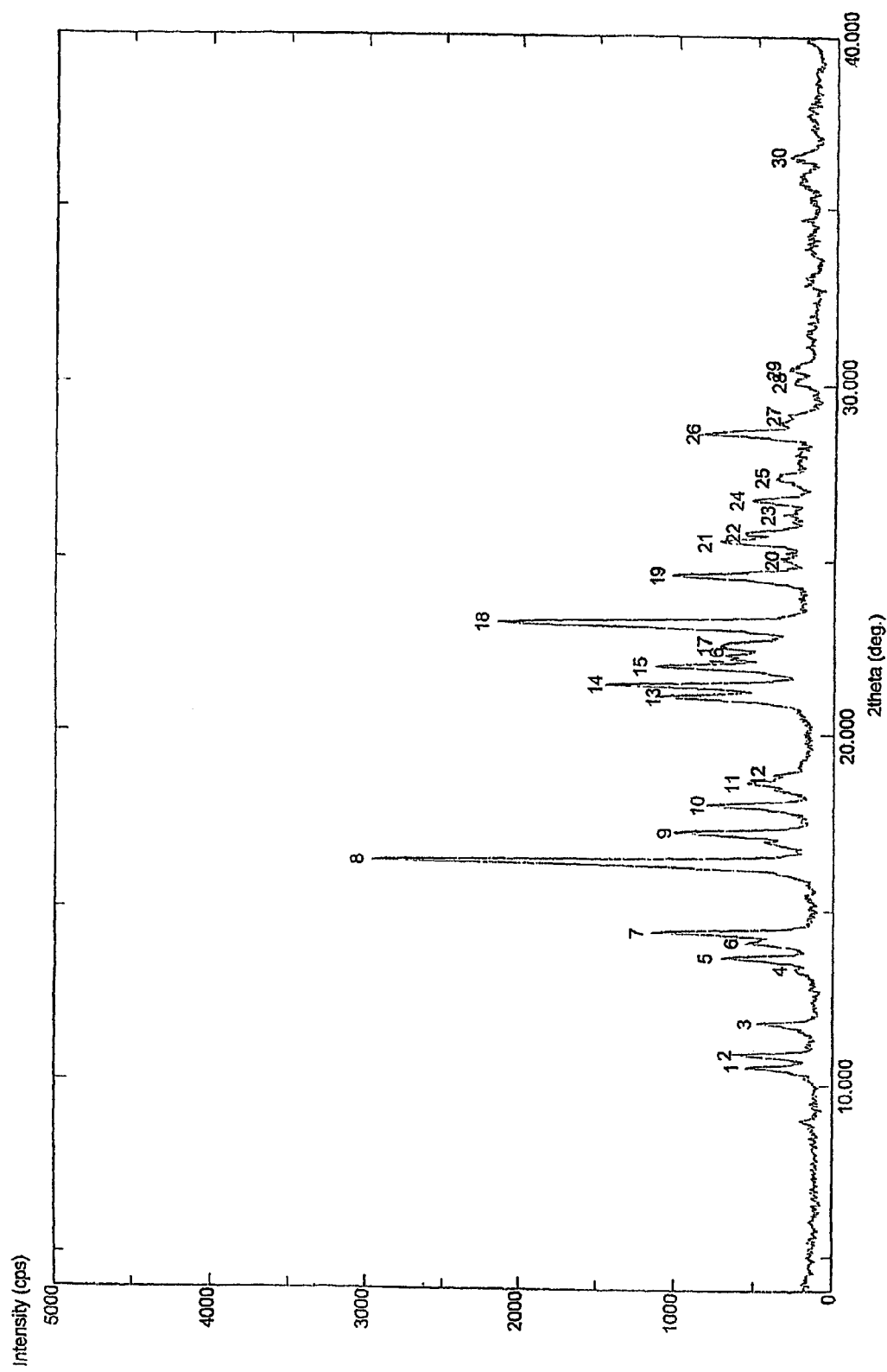
FIG. 2: XRD of crystalline Clopidogrel besylate
Figure 3:
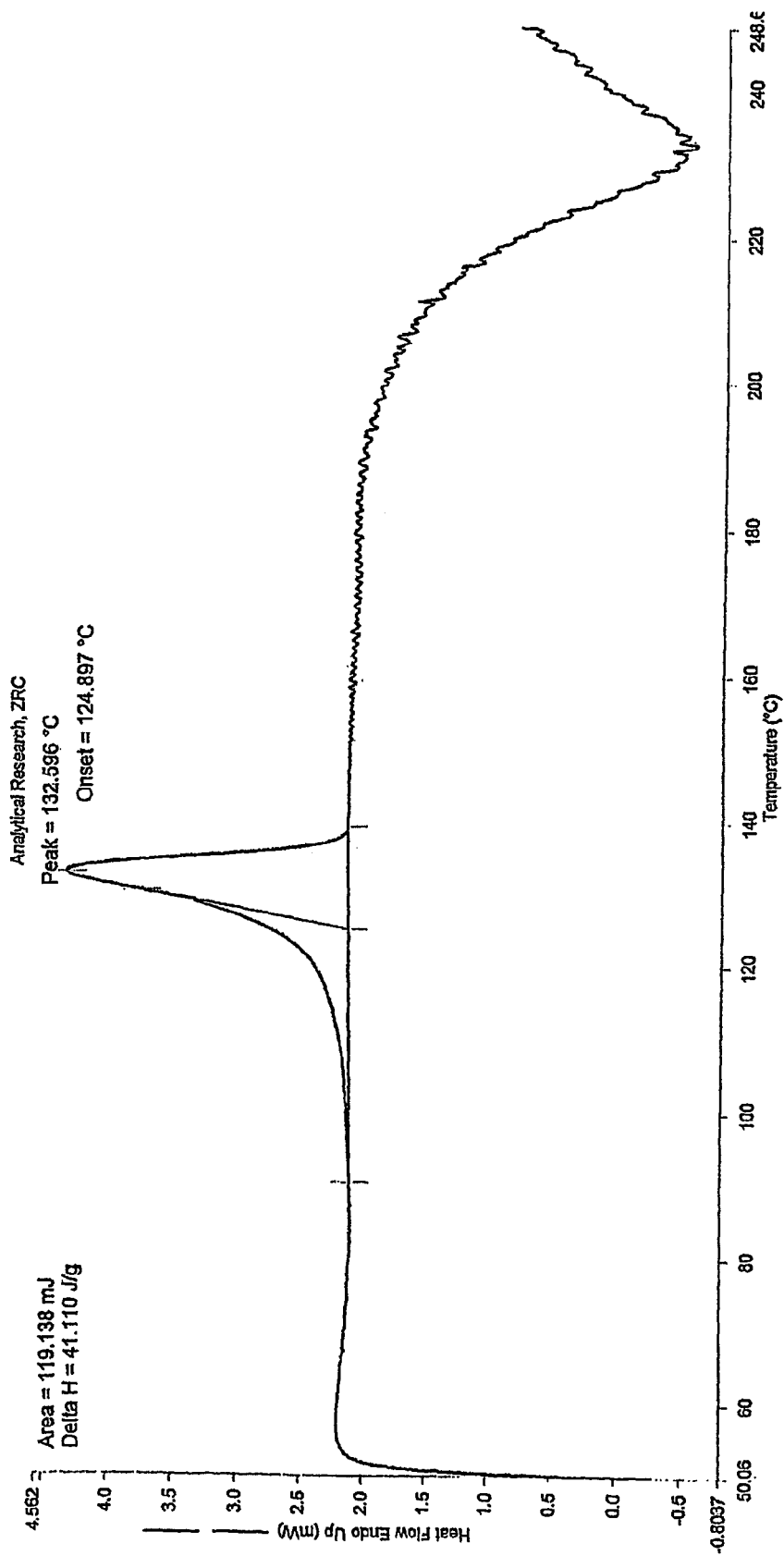
FIG. 3: DSC of crystalline Clopidogrel besylate
Figure 4:
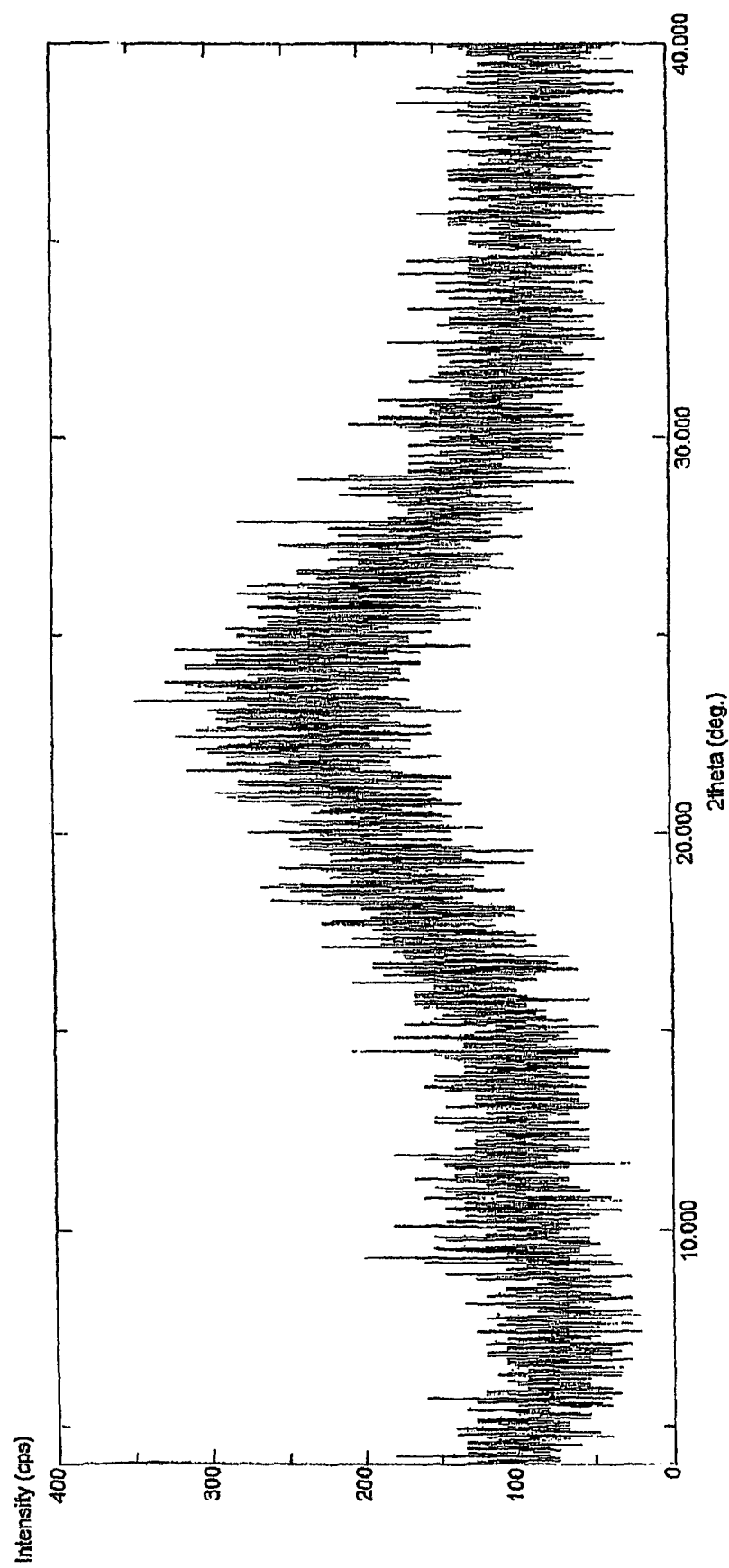
FIG. 4: XRD of amorphous Clopidogrel mesylate
Figure 5:
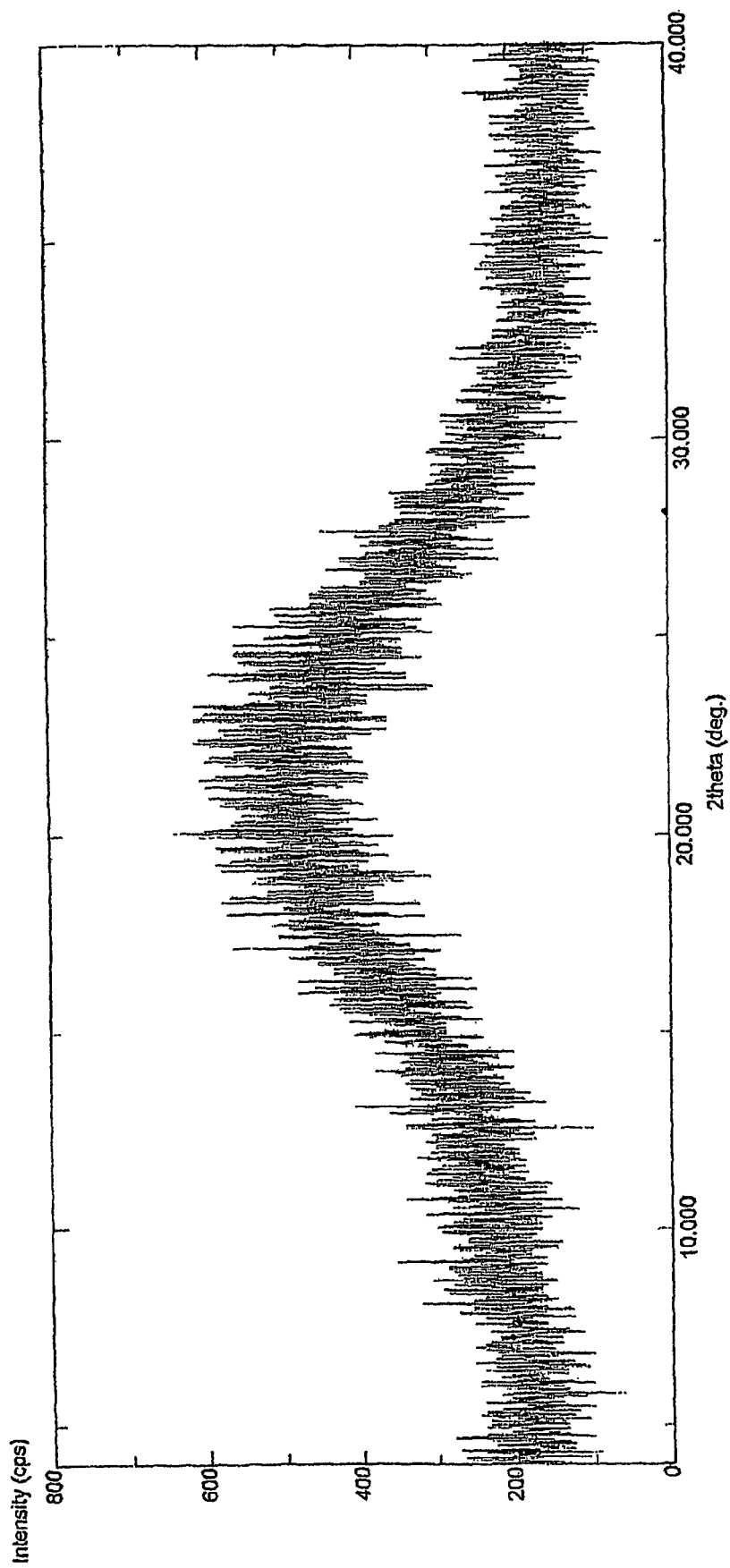
FIG. 5: XRD of amorphous Clopidogrel tosylate

We claim:

1. Crystalline Clopidogrel besylate having a powder X-ray diffraction pattern substantially as depicted in FIG. 2.

2. Crystalline Clopidogrel besylate as claimed in claim 1, which has a differential scanning calorimetric thermogram having an endothermic peak at about 124-134° C.

3. Crystalline Clopidogrel besylate as claimed in claim 1, which contains from about 0.1-0.3% water by weight.

4. A process for preparing crystalline Clopidogrel besylate having a powder X-ray diffraction pattern substantially as depicted in FIG. 2, comprising:
   i) dissolving/contacting Clopidogrel base in one or more solvents,
   ii) treating the product of step (i) with benzenesulfonic acid, and
   iii) removing the one or more solvents to obtain crystalline Clopidogrel besylate having a powder X-ray diffraction pattern substantially as depicted in FIG. 2.

5. The process as claimed in claim 4, wherein the one or more solvents are selected from the group consisting of water, n-heptane, cyclohexane, petroleum ether; ethers wherein each alkyl radical of the ether is independently selected from the group consisting of methyl, ethyl, propyl, isopropyl, butyl, 1-butyl, 2-butyl and t-butyl, and mixtures thereof.

6. A process for preparing crystalline Clopidogrel besylate having a powder X-ray diffraction pattern substantially as depicted in FIG. 2, comprising:
   i) dissolving/contacting amorphous Clopidogrel besylate in one or more solvents and
   ii) removing the one or more solvents to obtain crystalline Clopidogrel besylate having a powder X-ray diffraction pattern substantially as depicted in FIG. 2.

7. The process as claimed in claim 6, wherein the one or more solvents are selected from the group consisting of water, alcohols selected methanol, ethanol, propanol, n-butanol, acetone, acetonitrile, hexane, n-heptane, cyclohexane, petroleum ether, and ethers wherein each alkyl radical of the ether is independently selected from the group consisting of methyl, ethyl, propyl, isopropyl, butyl, 1-butyl, 2-butyl and t-butyl, and mixtures thereof.

8. The process as claimed in claim 6, wherein said amorphous Clopidogrel besylate has a powder X-ray diffraction pattern substantially as depicted in FIG. 1.

9. The process as claimed in claim 6, wherein said amorphous Clopidogrel besylate contains from about 0.5-4% water by weight.

* * * * *